United States Patent [19]
Carlson et al.

[11] Patent Number: 6,038,023
[45] Date of Patent: Mar. 14, 2000

[54] SENSORS FOR DETECTION AND SPECTROSCOPY

[75] Inventors: Bradley S. Carlson, Northport; Mikhail Gouzman, Lake Grove; Vera Gorfinkel, Stony Brook; Serge Luryi, Old Field, all of N.Y.

[73] Assignee: The Research Foundation of State University of New York, Stony Brook, N.Y.

[21] Appl. No.: 09/127,510

[22] Filed: Jul. 31, 1998

[51] Int. Cl.$^7$ ..................................................... G01J 3/18
[52] U.S. Cl. ............................................ 356/326; 356/328
[58] Field of Search .................................. 356/305, 308, 356/326, 328

[56] References Cited

U.S. PATENT DOCUMENTS

| | | | |
|---|---|---|---|
| 4,320,971 | 3/1982 | Hashimoto et al. | 356/328 |
| 4,958,928 | 9/1990 | Kuderer | 356/328 |
| 5,822,058 | 10/1998 | Adler-Golden et al. | 356/303 |

FOREIGN PATENT DOCUMENTS

| | | | |
|---|---|---|---|
| WO 91/03714 | 3/1991 | WIPO | 356/326 |

*Primary Examiner*—F. L. Evans
*Attorney, Agent, or Firm*—Baker Botts LLP

[57] ABSTRACT

For multicolor fluorescence detection or spectroscopy with low signal-to-noise ratio and rapid readout, signals from multiple sensors are combined in analog form so that only one signal per fluorescent response needs to be read from a sensor array. The contributions of sensors in the array to a given output signal are programmable, for exclusive selection of the desired information. As the contributions of sensors to output signals are electronically programmed, the energy of the light source can be filtered electronically. Such devices can be programmed in real time for adaptive measurements.

15 Claims, 5 Drawing Sheets

SENSORS FOR DETECTION AND SPECTROSCOPY

FIELD OF THE INVENTION

The invention relates to radiation detection and, more particularly, to spectral radiation detection.

BACKGROUND OF THE INVENTION

Electromagnetic radiation detectors and spectrometers are being used to measure the emission of radiation from samples of solids, liquids and gases. Typically, a sample is excited with suitable first radiation to stimulate the emission of second radiation, and the latter is analyzed to identify characteristics of the sample. This general principle is applied in medical imaging, DNA sequencing and other materials analysis, laser scanning, etc.

In a variety of applications it is important to measure the spectral content of electromagnetic radiation, for which purpose spectrometers and calorimeters are typically being used. Other applications involve spectral pattern recognition, wherein specialized signal processing is performed in addition to spectral measurements. In many applications, such as detection and identification of fluorescent objects, it is important to be able to measure selected bands of a received spectrum, and it is often advantageous to be able to change the selection of the measured bands in the course of the measurement.

To measure selected spectral bands, certain known devices scan a dispersed spectrum, or apply signal processing of a spectral image obtained by optical dispersion. Both of these techniques suffer from being relatively slow, so that they are inconvenient where rapidly varying spectral information needs to be processed, such as, e.g., information obtained in spectroscopy of modulated radiation.

SUMMARY OF THE INVENTION

For rapid reconfiguration of signals corresponding to different spectral bands of received electromagnetic radiation, a preferred technique in accordance with the invention provides for grouping of several selected spectral bands. Signals from selected sets of pixels of a photo-receiving array or matrix are combined into one or several registration paths.

DETAILED DESCRIPTION OF PREFERRED EMBODIMENTS

For specificity and exemplification, preferred sensors are described in the following for optical detection and spectroscopy of fluorescence. Applications within the scope of the invention further include sensors for other types of electromagnetic radiation, as well as for non-radiative quantities such as gas concentrations, for example.

Figure 1:
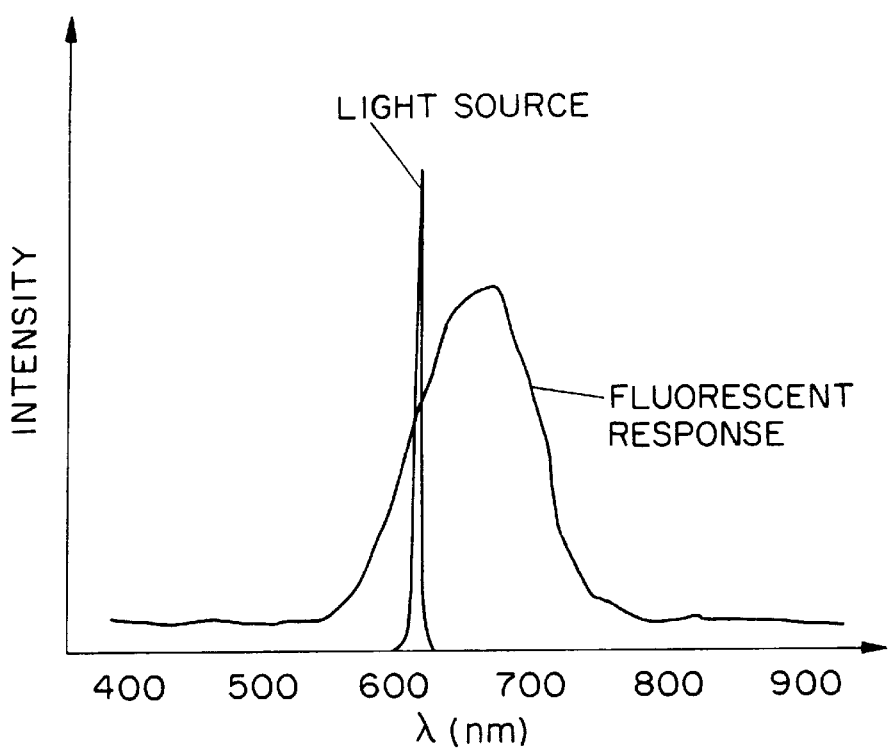
FIG. 1 is a graphic representation of typical fluorescent response of a solid, liquid or gas sample.

Excitation of a fluorescent sample produces fluorescence. A fluorescent sample may be excited by an external modulated light source such as a laser, for example, and generate a modulated fluorescent signal in response. A fluorescent sample may be naturally fluorescent, or become fluorescent when fluorescent markers (fluorophores) are added. The characteristic fluorescence can be used to determine the material composition, e.g., to detect when fluorophores are added to a solution, to identify the fluorescent species added, and to quantify the amount of the added species. A typical fluorescent response of a solid, liquid or gas sample is shown in FIG. 1. The sample is excited by the laser source and the fluorescent response is produced by the atomic interaction of the light and the sample. The fluorescent response can be acquired using an optical spectrometer. The wavelength of the light source is controlled, and the response is measured using an optical spectrometer or detector. An optical spectrometer divides the optical spectrum into discrete spectral bands and collects photons from each of the bands. The spectrometer outputs a sequence of electrical signals corresponding to the intensity of light in each spectral band. Using terminology from electronic imaging, such a sequence of electrical signals will be referred to as a frame of data. This sequence of signals can be processed to produce a diagram similar to that of FIG. 1.

While the inventive technique is described in the following primarily in the instance of stimulated fluorescence, other forms of stimulated optical response are not precluded, such as reflection, transmission, Raman and the like. Furthermore, the inventive technique can be applied advantageously to measurement of the spectral composition of various types of radiation, especially radiation whose spectral composition varies in time.

Figure 2:
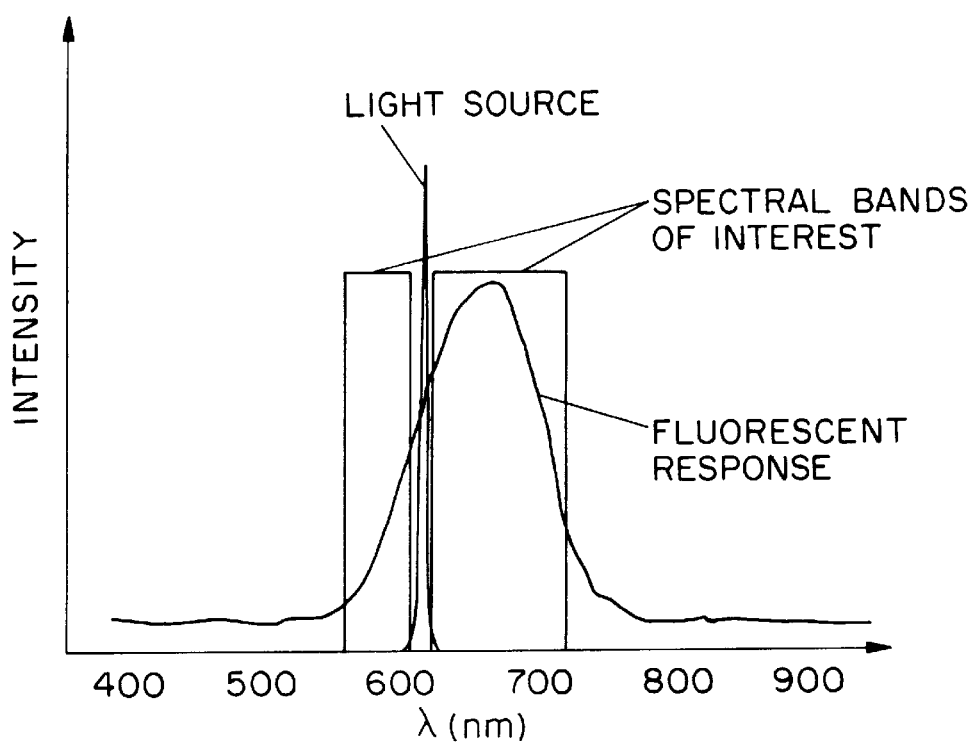
FIG. 2 is a graphic representation of the fluorescent response according to FIG. 1, further illustrating selected spectral bands of interest.

An optical detector differs functionally as compared to an optical spectrometer. While the spectrometer's purpose is to faithfully account for the distribution of light intensities over a spectral region, the purpose of an optical detector is to measure the total intensity received in its optical input. The optical input may comprise a narrow spectral region, a wide spectral region, or a plurality of spectral bands having different widths. Typically, an optical detector has higher sensitivity in specialized spectral regions. For many applications it may be advantageous to combine the spectral resolution of a spectrometer with the sensitivity of an optical detector. For example, in the case of fluorescent response, one is often interested in a spectral shape as illustrated in FIG. 2, comprising the entire fluorescent response except for a region around the laser line that has caused the fluorescent response.

The output signals of the spectrometer corresponding to the spectral bands of interest can be accumulated external to the sensor. In known spectrometers it is necessary to read the entire sequence of signals from the spectrometer, from which signals of interest are then selected. Single, discrete optical detectors are not ideal for fluorescence detection because the wavelength of the laser source often falls within the spectral sensitivity of the detector. Optical filtering is necessary to suppress the radiation of the laser. In addition, the spectral response of discrete optical detectors is difficult to control.

Figure 3:
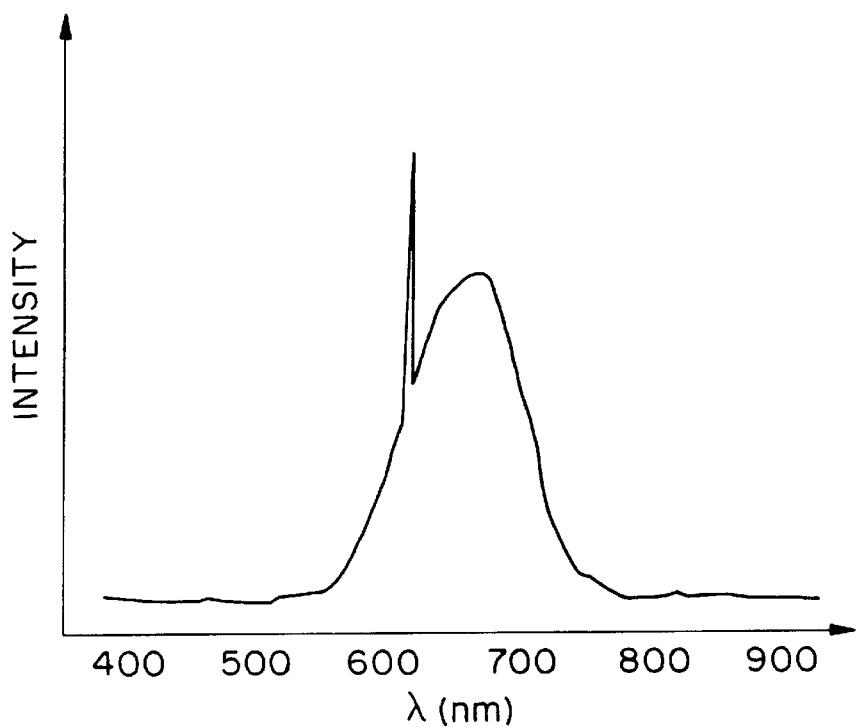
FIG. 3 is a graphic representation of data acquired by a prior-art spectrometer based on the fluorescent response according to FIG. 1.

Known modular spectrometers utilizing charge-coupled device (CCD) sensors include optics that spatially distributes the light by wavelength over a linear CCD sensor, with each pixel in the line sensor collecting photons in a given spectral band. To measure the fluorescence of a sample, the entire CCD array is read out and signal processing is performed on a digital computer. FIG. 3 shows the response of this type of spectrometer to the fluorescence in FIG. 1.

Although many of the pixels of the sensor collect photons from background noise only, and are not useful for the measurement desired, the nature of the CCD requires that all pixels be read. Also, the spatial resolution of the CCD is fixed, so that many pixels collect photons from the same fluorescent response and must be accumulated outside the spectrometer. Furthermore, digital processing is required to separate the energy of the laser source from the energy of the fluorescence.

In recent years the use of CMOS (complementary metal oxide semiconductor) technology has received attention for the implementation of image sensors, e.g. for general purpose imagers and vision systems. CMOS imaging systems have several advantages which include lower cost and higher frame rate, which is important for imaging rapidly moving pictures and for handling temporally modulated radiation. Another technical advantage of CMOS imagers is the absence of interference between nearby pixels which is due to electric charge spreading inherent in many CCD designs.

A particular further advantage of CMOS imagers is that they permit rapid reconfiguration of the sensor, as well as flexible control and signal processing. As a result, CMOS imagers have proven useful in vision systems, where it is important to adapt to wide and rapid variations in lighting conditions.

Figure 4:
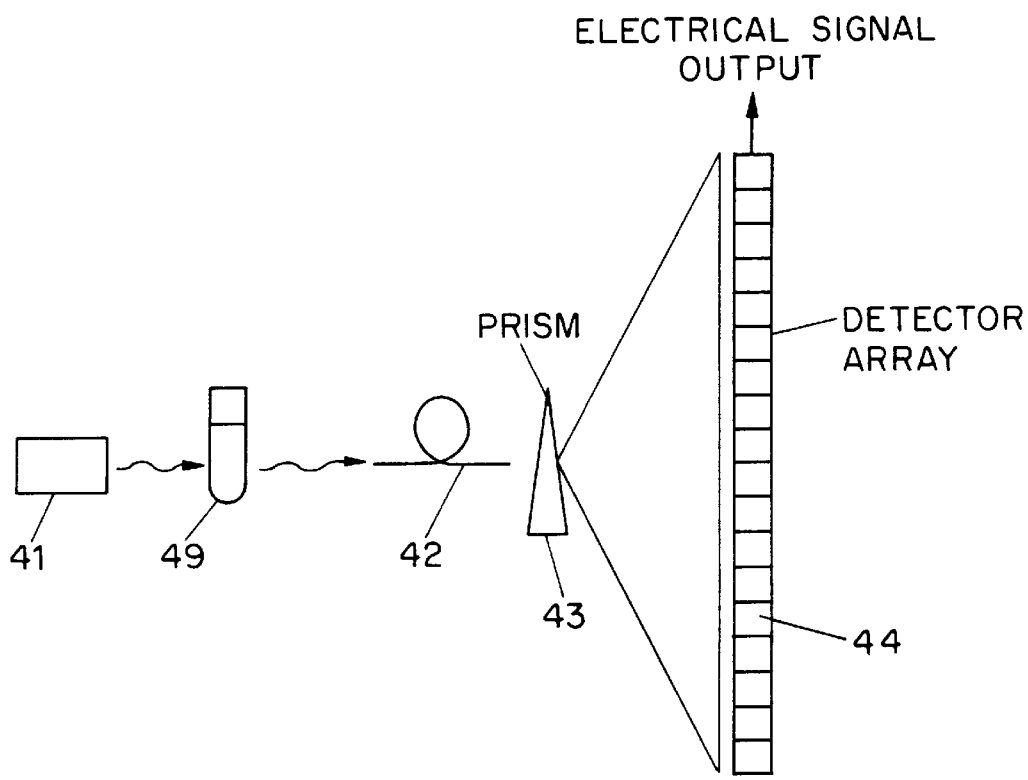
FIG. 4 is a schematic of a fluorescent spectrometer.

The fluorescent spectrometer of FIG. 4 is shown with a source 41 of radiation for stimulating fluorescence in a sample 49, an optical fiber 42 for receiving fluorescent radiation, a prism 43, and a detector array 44 for producing an electrical signal output. Known spectrometers, e.g. Ocean Optics, Model 2000, utilize a CCD detector array. The spectral resolution is fixed by the characteristics of the dispersive element exemplified by the prism 43, and can be changed only by manually retrofitting the device with a new dispersive element.

Preferred detectors and spectrometers in accordance with the invention are advantageous over known CCD-based spectrometers in that the width of the spectral bands is programmable, and only those signals which are useful for a desired measurement are read out of the spectrometer. The photons from any set of spectral bands can be collected and read out as one signal. The width of the spectral bands selected need not be uniform across the array. Thus, photons from multiple fluorescent responses can be collected simultaneously, and the spectral bands can be selected to optimize signal-to-noise ratio.

Figure 5:
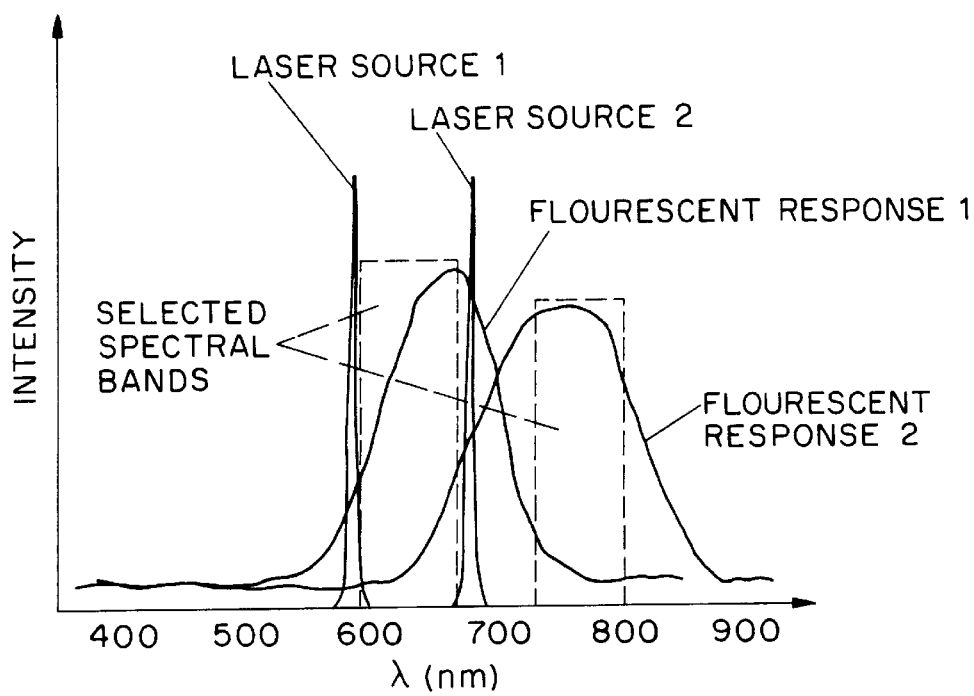
FIG. 5 is a graphic representation illustrating selection of spectral bands to optimize signal acquisition for multiple fluorescent responses.

In accordance with an aspect of the invention, a sensor can be programmed such that any number of signals corresponding to selected spectral bands are read out of the spectrometer, e.g. so that only one electrical signal per fluorescent response is read out per frame. For example, as illustrated by FIG. 5, the spectrometer can be programmed such that a frame of data contains only two signals, one for each of two fluorescent responses. Furthermore, each signal contains information from multiple sensors so the signal-to-noise ratio can be optimized and the energy of the laser source can be filtered electronically. The acquisition time compared to a CCD sensor is improved by several orders of magnitude, because only the signals of interest need to be read from the sensor array. The device can be programmed automatically from the information of one entire frame of data. During an experiment, such as DNA sequencing by electrophoresis, the device can be re-programmed in real time to adapt to changing experimental conditions such as drift of fluorescent wavelengths (e.g., due to temperature variations) and instabilities of the light source excitation spectrum, such as temperature instabilities known to occur in semiconductor lasers.

The invention is particularly advantageous when the excitation source is modulated. The sensor and read-out circuitry can be designed to operate in continuous-time mode, permitting straightforward demodulation of the collected radiation signal. This advantage may be appreciated especially vis-a-vis CCD-based devices which are inherently discrete-time due to their method of photo-electric conversion which makes demodulation of collected radiation difficult. To obtain functionality similar to that of the invention, a CCD-based spectrometer would have to be coupled to a digital computer with custom software for signal processing, amounting to orders of magnitude more resources. In accordance with an aspect of the invention, optical band selection requires minimal hardware for real-time readout of selected information only, without readout of extraneous information. The selection can be changed simply by writing new control information into the control register, in real time.

For sensing electromagnetic radiation, sensor devices are not restricted as to type or spectral sensitivity. For example, sensors with continuous-time mode of photoelectric conversion such as photo diodes can be used, and sensitivity may lie outside the visible and near-infrared wavelength range of a CCD-based system.

Programmable Multiwavelength Detector

The systems described in the following generally use an optical system of the type depicted in FIG. 4. The light source is interfaced to the system by fiber optical or other means, and the light is distributed in the optical spectrum using a prism or a diffractive element and focused onto a detector or sensor array. Novel sensor arrays in accordance with the invention significantly improve the performance and flexibility of such systems for multiwavelength detection and spectroscopy. The new sensor architecture can be used with any array of sensors, which can be integrated with sensor read-out electronics on the same crystal of silicon in the case of visible-light silicon p-n junction or silicon photogate sensors. The sensor array can also be separate from the read-out electronics and interfaced to it using known bonding and assembly techniques. Suitable read-out electronics are included depending on the sensor type, e.g., for visible or non-visible electromagnetic radiation sensors, chemical sensors, magnetic sensors, acoustic sensors, and the like. In the specific embodiments described below, sensor arrays are linear, but different arrangements are not precluded, such as two dimensional arrays, for example.

Figure 6:
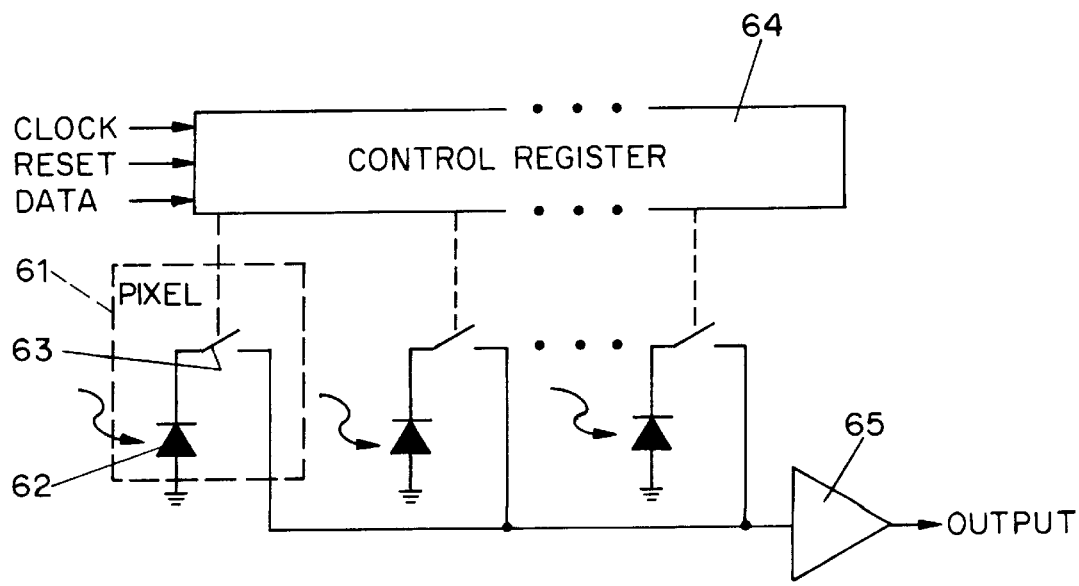
FIG. 6 is a block diagram of a multicolor detector in accordance with a preferred first embodiment of the invention.

As shown in FIG. 6, each pixel 61 contains a photosensitive element 62 and a switch 63 that is controlled by the content of a binary memory element in the control register 64. A set of pixels, not necessarily contiguous, or spectral bands are selected by writing a bit pattern to the control register. The photocurrents of the selected pixels are summed at the input of the amplifier 65. Antiblooming techniques can be used so that electron-hole pairs excited by the absorption of photons in unselected pixels recombine without affecting neighboring pixels. The elements 62 can be operated in integrating mode or continuous mode, and the amplifier can be integrated on-chip with the sensors or connected external to the chip. The control circuitry can be implemented in CMOS technology, and the photosensitive elements can be implemented in CMOS also, in forming a monolithic device, or in any other suitable sensor technology, in forming a hybrid device.

Information from several fluorescent responses can be encoded in a single electrical signal and decoded electronically. E.g., the light sources for each fluorescent response can be modulated at different frequencies. The spectral bands corresponding to each fluorescent response can be selected for read-out, and the electrical signals are encoded according to the modulation frequencies of the light sources. The separate signals can be decoded from the read-out signal with the knowledge of the modulation frequency.

Figure 7:
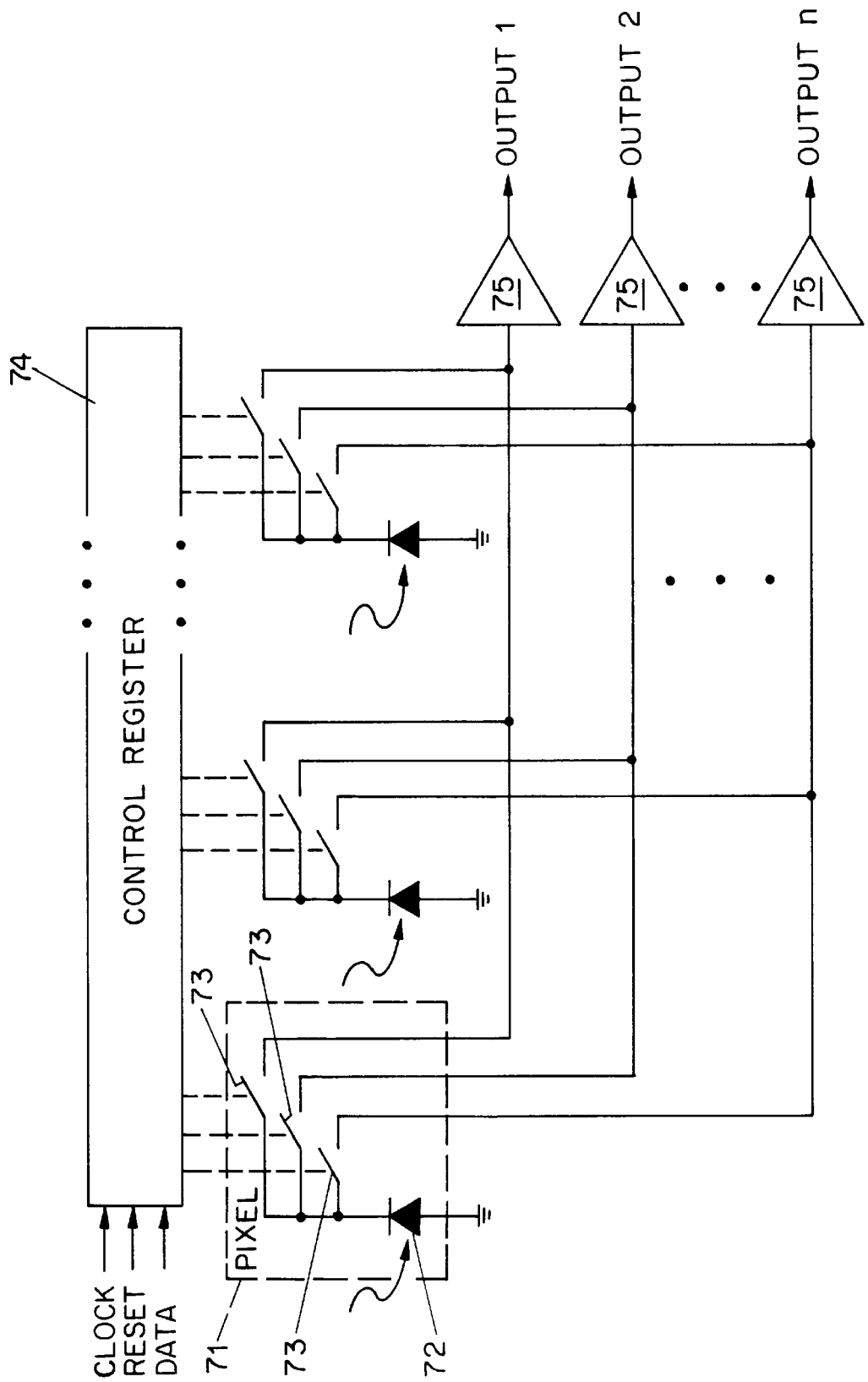
FIG. 7 is a block diagram of a multicolor detector for detecting responses from multiple fluorophores in accordance with a preferred second embodiment of the invention.

For simultaneous and independent readout of several spectral bands, 1 to n, FIG. 7 shows each pixel 71 having a photosensitive element 72 and n switches 731 to 73n. The switches are under the control of bits in a bit pattern in the control register 74. Separate amplifiers 751 to 75n are associated with the pixels. A single pixel can be selected to contribute to any number of outputs, and the number of outputs is limited only by the pin-out of the packaging technology. This is on the order of hundreds for current packaging technologies. Photosensitive elements can be in CMOS or in a more sensitive technology, for example. The photosensors 72 can be continuous-time photodetectors, and the output amplifiers 751 to 75ncan be on or off chip.

Programmable Spectrometer

Figure 8:
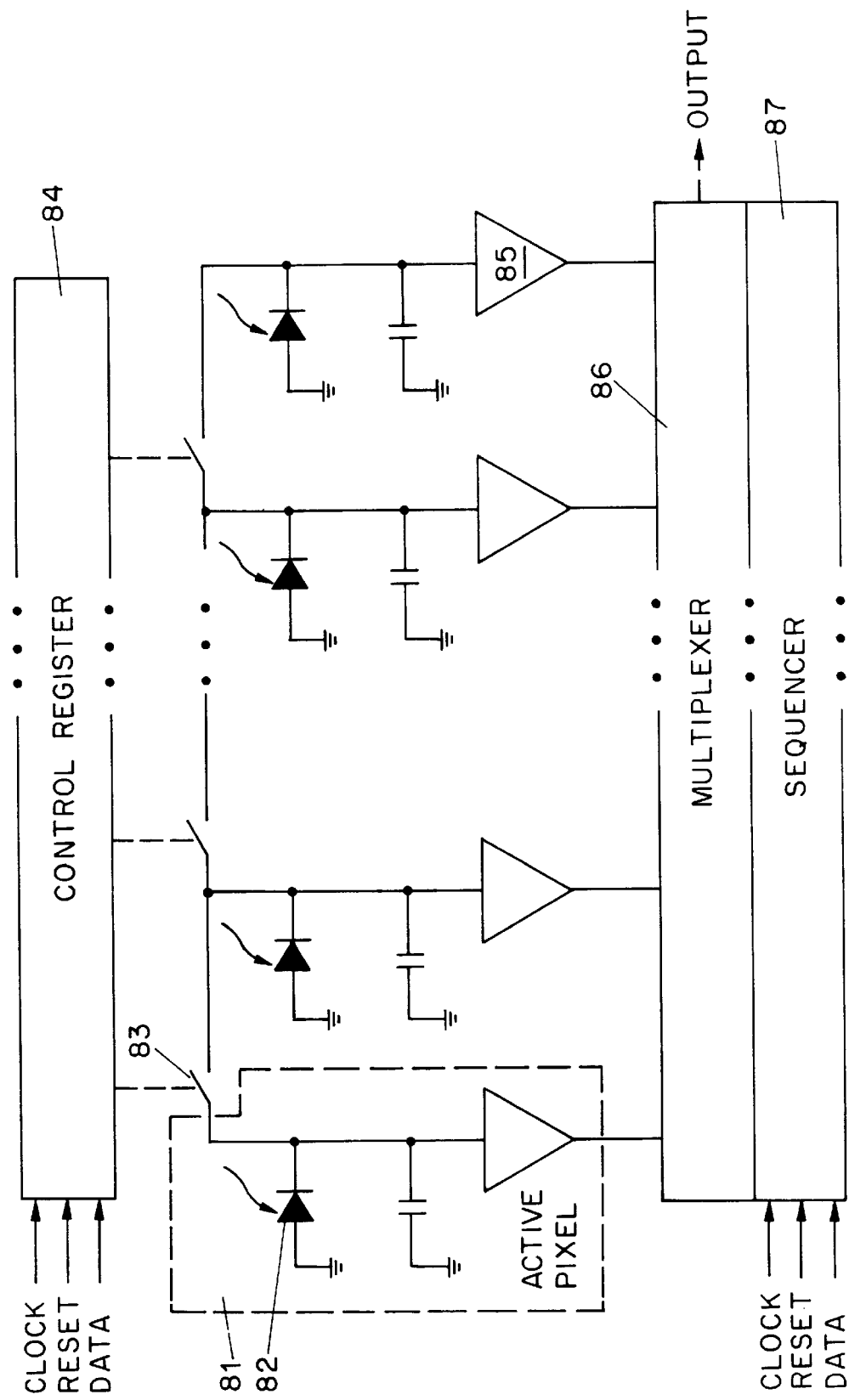
FIG. 8 is a block diagram of a programmable spectrometer in accordance with a preferred third embodiment of the invention.

FIG. 8 illustrates a programmable spectrometer which can be programmed to control spectral resolution and read-out. The spectrometer includes a row of photosensitive elements 82 for pixels 81, and control circuitry including switches 83, a control register 84 as described above for FIGS. 6 and 7, amplifiers 85, a multiplexer 86, and a sequencer 87. For a two-dimensional array of pixels, the control register bit can be included within the pixel. The photosensors operate in an integrating mode or a continuous mode. A bit pattern is written to the control register 84 to select the spatial resolution. If the switch between two pixels is closed, the signals induced by the photons incident on both sensors contribute to the same output signal. Spectral bands of arbitrary width can be selected, but only adjacent pixels can be selected to contribute to an output signal. For a sensor with 100 pixels, and with light spread over an optical band 100 nm wide, the optical spatial resolution of the sensor is 1 nm per pixel. If the switches between k adjacent pixels are closed, then the acquired signal corresponds to the accumulation of photons in an optical band k×1 nm wide. The sequencer 87 controls signal read-out of the pixel array using virtual addressing. It is initialized with a count and a set of addresses corresponding to the sets of pixels to be read. One frame of read-out consists only of those pixels whose addresses are stored in the sequencer. To read the signal from a group of pixels, any one of the pixels in the group can be selected by the sequencer.

We claim:

1. A detector comprising:

a diffractive element which is configured and disposed for receiving electromagnetic radiation and for generating a spectrum from the received electromagnetic radiation;

a plurality of radiation-sensitive elements wherein each radiation-sensitive element is disposed and configured to receive a different portion of the spectrum and to generate a signal depending on radiation in its portion of the spectrum;

a control means configured for holding a control entry for each of the radiation-sensitive elements, operationally coupled to the radiation-sensitive elements such that each of the radiation-sensitive elements is operationally coupled for outputting its signal depending on the status of its control entry; and a multiplexer operationally coupled for multiplexing the output signals from the radiation sensitive elements.

2. The detector according to claim 1, wherein the diffractive element comprises a prism.

3. The detector according to claim 1, wherein the diffractive element comprises a grating.

4. The detector according to claim 1, configured for outputting the signals from the radiation-sensitive elements individually.

5. The detector according to claim 1, configured for combining the signals from the radiation-sensitive elements whose signals are being outputted.

6. The detector according to claim 5, wherein combining comprises adding.

7. The detector according to claim 1, configured for combining selected ones of the signals from the radiation-sensitive elements onto selected ones of a plurality of outputs.

8. The detector according to claim 7, wherein combining comprises adding.

9. The detector according to claim 7, wherein each of the selected ones of the signals from the radiation-sensitive elements is combined onto exactly one of the plurality of outputs.

10. The detector according to claim 9, wherein combining comprises adding.

11. The detector of claim 7, wherein at least some of the selected ones of the signals from the radiation-sensitive elements are combined onto more than one of the plurality of outputs.

12. The detector according to claim 11, wherein combining comprises adding.

13. The detector according to claim 1, wherein the control means comprises a control register.

14. The detector according to claim 13, wherein the control means comprises a plurality of switching devices, with each switching device being operationally coupled to an entry in the control register.

15. The detector according to claim 14, wherein each switching device comprises a CMOS.

\* \* \* \* \*

UNITED STATES PATENT AND TRADEMARK OFFICE
CERTIFICATE OF CORRECTION

PATENT NO. : 6,038,023

DATED : March 14, 2000

INVENTOR(S) : Bradley S. Carlson et al.

It is certified that error appears in the above-identified patent and that said Letters Patent is hereby corrected as shown below:

Col. 1, after the Title, insert -- The United States Government has certain rights in this invention pursuant to Grant No. HG01487 awarded by the NIH. --.

Signed and Sealed this

Twentieth Day of February, 2001

Attest:

NICHOLAS P. GODICI

Attesting Officer

Acting Director of the United States Patent and Trademark Office